(12) United States Patent
Lal et al.

(10) Patent No.: US 6,515,191 B2
(45) Date of Patent: Feb. 4, 2003

(54) SYNTHESIS OF VICINAL DIFLUORO AROMATICS AND INTERMEDIATES THEREOF

(75) Inventors: Gauri Sankar Lal, Whitehall, PA (US); Kathryn Sue Hayes, Plymouth Meeting, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/197,969

(22) Filed: Jul. 17, 2002

(65) Prior Publication Data

US 2002/0198417 A1 Dec. 26, 2002

Related U.S. Application Data

(60) Division of application No. 09/985,786, filed on Nov. 6, 2001, now Pat. No. 6,455,744, which is a continuation-in-part of application No. 09/767,636, filed on Jan. 23, 2001, now abandoned.

(51) Int. Cl.[7] .............................................. C07C 25/22
(52) U.S. Cl. ..................................................... 570/143
(58) Field of Search .................................. 570/123, 143

(56) References Cited

U.S. PATENT DOCUMENTS

| | | | |
|---|---|---|---|
| 5,498,807 A | 3/1996 | Schach et al. | 570/127 |
| 5,900,502 A | 5/1999 | Skinner et al. | 558/303 |
| 6,008,407 A | 12/1999 | Nefedov et al. | 562/422 |

FOREIGN PATENT DOCUMENTS

| | | | |
|---|---|---|---|
| JP | 10995 A | 1/2001 | C07C/25/22 |

OTHER PUBLICATIONS

N. Yoneda and T. Fukuhara, *Tetrahedron*, vol. 52, No. 1 (1996), pp. 23–36.
C. Hu, et al., *Journal of Fluorine Chemistry*, vol. 48 (1990), pp. 29–35.
J. Burdon and I. W. Parsons, *Journal of Fluorine Chemistry*, vol. 13 (1979), pp. 159–162.
Sergey S. Laev and Vitalii D. Shteingarts, *Journal of Fluorine Chemistry*, vol. 96 (1999), pp. 175–185.
Mark W. Briscoe, et al., *J. Chem. Soc., Chem. Commun.*, (1990), pp. 1127–1128.
Antonella Profumo, et al., *Heterocycles*, vol. 51 (Nov. 7, 1999), pp. 1499–1502.

Primary Examiner—Joseph K. McKane
Assistant Examiner—Golam M M Shameem
(74) Attorney, Agent, or Firm—Mary E. Bongiorno

(57) ABSTRACT

A method of preparing vicinal difluoro aromatic compounds in high yield from hydroxy aromatic compounds and a method of preparing intermediates thereof. The hydroxy aromatic compound can be a mono-, bi- or tricyclic aromatic in which the rings are separate or fused. One or more of the rings can contain heteroatoms, such as oxygen, nitrogen, or sulfur, and can contain one or more substitutions, in addition to the hydroxy substitution.

8 Claims, No Drawings

SYNTHESIS OF VICINAL DIFLUORO AROMATICS AND INTERMEDIATES THEREOF

CROSS REFERENCE TO RELATED APPLICATIONS

This application is a division of U.S. application Ser. No. 09/985,786, filed on Nov. 6, 2001, U.S. Pat. No. 6,455,744 which is a continuation-in-part of U.S. Application Ser. No. 09/767,636, filed on Jan. 23, 2001, abandoned.

BACKGROUND OF THE INVENTION

Aromatic compounds, especially naphthalene derivatives, bearing fluorine atoms on adjacent carbons (i.e., vicinal) have been found to be useful as liquid crystal materials. They are typically made by a multi-step process, starting from the aromatic amine via a fluoro-dediazoniation process (N. Yoneda and T. Fukuhara, *Tetrahedron,* vol. 52, No. 1 (1996), pages 23–36).

No simple methods are known for producing vicinal difluoro aromatic compounds. Methods for defluorinating highly fluorinated compounds are known; but, none of the methods have been shown to produce vicinal difluoro compounds in high yield. For example:

C. Hu, et al., *Journal of Fluorine Chemistry,* Vol. 48 (1990), pages 29–35, disclosed a method of synthesizing perfluoroaromatics, such as tetradecafluorobicyclo[4.4.0]dec-1 (2),6(7)-diene and perfluorotetralin, by defluorination of hexadecafluorobicyclo[4.4.0]dec-1 (6)-ene in an aprotic solvent using activated zinc powder as a catalyst. The extent of defluorination depended on the polarity of the aprotic solvent used.

J. Burdon and I. W. Parsons, *Journal of Fluorine Chemistry,* Vol. 13 (1979), pages 159–162, disclose the formation of 2,5-difluorothiophen by pyrolysis of 2,2,5,5-tetrafluoro-3-thiolen over sodium fluoride.

Sergey S. Laev and Vitalii D Shteingarts, *Journal of Fluorine Chemistry,* Vol. 96 (1999) pages 175–185, disclose the reductive dehalogenation of polyfluoroarenes by zinc in aqueous ammonia. In the reaction, hydrogen atoms replace fluorine atoms in the polyfluoroarenes.

JP 2001–10995A (Ogawa, et al.) describes a four-step process for synthesis of vicinal difluoro aromatic compounds involving fluorination of a hydroxy aromatic compound to form a tetrafluoro intermediate in two steps followed by hydrogenation and defluorination under basic conditions. It also discloses reduction of a difluoroketone intermediate with aluminum isopropoxide and then base-catalyzed dehydrohalogenation to form a difluoro aromatic compound. A third method involves reaction of the difluoroketone with lithium aluminum hydride to form a fluoroepoxide, addition of HF, and elimination of water to give a vicinal difluoro aromatic compound. The best overall yield shown is <50%.

There remains a need for an effective and simple method for preparing vicinal difluoro aromatic compounds in high yield.

BRIEF SUMMARY OF THE INVENTION

This invention is directed to a method of preparing vicinal difluoro aromatic compounds in high yield from hydroxy aromatic compounds and to preparing intermediates thereof. The hydroxy aromatic compound can be a mono-, bi- or tricyclic aromatic in which the rings are separate or fused. One or more of the rings can contain heteroatoms, such as oxygen, nitrogen, or sulfur, and can contain substitutions, in addition to the hydroxy substitution. Substitutions on one or more of the rings can include a halogen atom, a C1 to C20 alkyl, a C5–C10 cycloalkyl, a C6 to C12 aryl, an amino, a nitro, a C1 to C10 alkyl ether or thioether, a C1 to C10 alkyl ester, a $CF_3$, a $R'SO_2O$,

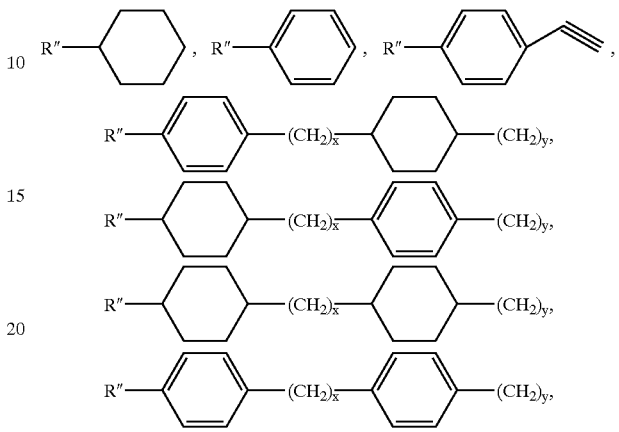

where R' is $CF_3$, a C1 to C20 alkyl, a substituted or unsubstituted C5 to C10 cycloalkyl, or a substituted or unsubstituted C6 to C12 aryl, in which the substitution on the cycloalkyl or aryl can be a C1 to C20 alkyl or a C5 to C8 cycloalkyl; R" is a C1–C10 saturated or unsaturated alkyl; x is an integer from 0 to 10, and y is an integer from 0 to 10.

The process can be described by the following reaction steps:

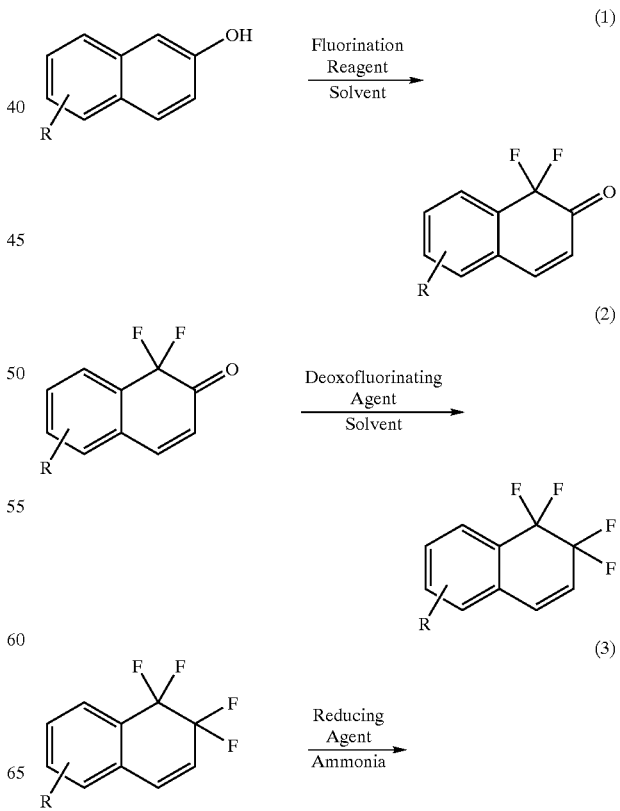

-continued

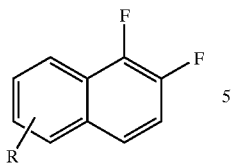

where R is a hydrogen atom, a halogen atom (Cl, Br, I, F), R'SO$_2$O, CF$_3$, a fused aryl, a C1–C20 alkyl, amino, nitro, a C1 to C10 ether or thioether, a C1 to C10 ester, a heteroaryl, wherein the heteroatom can be O, N, S,

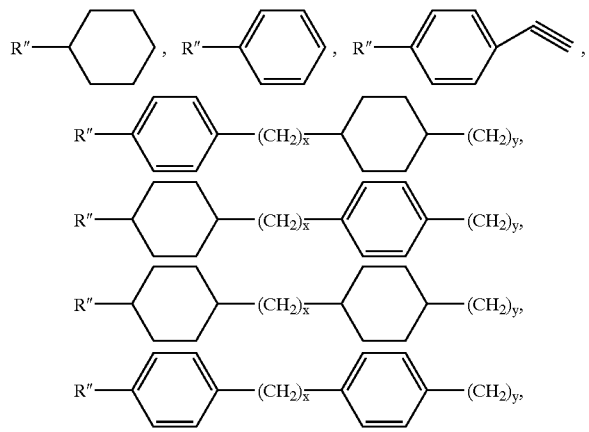

or R forms an aryl.

R" is CF$_3$, a C1 to C20 alkyl, a substituted or unsubstituted C5 to C10 cycloalkyl, or a substituted or unsubstituted C6 to C12 aryl, wherein the substitution on the cycloalkyl or aryl can be a C1 to C20 alkyl or a C5 to C8 cycloalkyl; R"' is a C1–C10 saturated or unsaturated alkyl; x is an integer from 0 to 10, and y is an integer from 0 to 10. The preferred R group is trans-4-propylcyclohexyl.

The yields obtained from reactions (1) and (2) are highly dependent on the solvents employed for these steps. Polar aprotic solvents are desirable for the electrophilic fluorination in step (1) and dimethylformamide (DMF) is particularly preferred because it unexpectedly resulted in yields of greater than 95% difluoro ketone product. Reaction step (2) can be conducted in various solvents including aliphatic and aromatic hydrocarbons, halocarbons, ethers, etc.; however, toluene unexpectedly gives much higher yields of the tetrafluoro product compared to other organic solvents. Step (3) involves reacting the tetrafluoro compound with a reducing agent, such as metallic zinc, copper, magnesium, or a mixture thereof, to form the vicinal difluoro aromatic compound in high yields (e.g., 90% or more). This reaction is preferably carried out in buffered aqueous ammonia in the presence of an organic solvent such as tetrahydrofuran (THF), methyl tert-butyl ether, acetonitrile, ethanol, or DMF. Since the tetrafluoro compound reacts under basic conditions to form a trifluoronaphthalene by-product, the pH of the aqueous ammonia is buffered to <14 by addition of an ammonium salt, particularly NH$_4$Cl. Under these conditions, the selectivity to the desired vicinal difluoronaphthalene product is significantly increased.

This method of preparing vicinal difluoro aromatic compounds has the following advantages over known methods:
the difluoro ketone and tetrafluoro intermediates do not need to be purified prior to subsequent reaction,
the product is produced in high selectivity,
the overall yield is 70% or more, and
the product easily can be separated and purified by known methods.

DETAILED DESCRIPTION OF THE INVENTION

In the method of this invention, vicinal difluoro aromatic compounds can be prepared in three steps from hydroxy aromatic compounds by electrophilic fluorination using a fluorination reagent such as Selectfluor® reagent (1-chloromethyl-4-fluoro-1,4-diazabicyclo[2.2.2]octane bis-tetrafluoroborate) to form a difluoroketone intermediate. The difluoro ketone undergoes nucleophilic fluorination by reaction with a deoxofluorinating reagent such as Deoxo-Fluor® reagent (bis(2-methoxyethyl)-aminosulfur trifluoride) to give a tetrafluoro intermediate species. The tetrafluoro intermediate is defluorinated by a metallic reducing agent in the presence of ammonium hydroxide, preferably buffered ammonium hydroxide, to provide the desired vicinal difluoro aromatic compound in high yield. An example of the reaction chemistry is described above in the Brief Summary of the Invention.

In the first step, a hydroxy aromatic compound (e.g., β-naphthol or substituted naphthol) is reacted with an electrophilic fluorinating agent such as Selectfluor reagent, to generate a difluoroketone intermediate. This reaction can be conducted in various solvents including nitrites such as acetonitrile (CH$_3$CN), formamides such as dimethylformamide (DMF), CH$_3$NO$_2$, carboxylic acids such as acetic acid, water, and an alcohol such as methanol, ethanol, and propanol.

The reaction can be carried out at temperatures ranging from 0° C. to the boiling point of the solvent.

The fluorinating agent can be added to a solution or suspension of the hydroxy aromatic compound in one or more portions, or dropwise as a solution. Alternatively, the hydroxy aromatic compound solution or suspension can be added to a solution or suspension of fluorinating agent.

In the second step, the carbonyl oxygen of the difluoroketone is replaced by two fluorine atoms using a deoxofluorinating agent such as Deoxo-Fluor reagent. The reaction is carried out by reacting the difluoroketone with the deoxofluorinating agent in an organic solvent in an anhydrous atmosphere. Solvents include alkanes such as hexane, heptane, etc.; aromatic hydrocarbons such as toluene, xylenes, etc.; haloalkanes such as methylene chloride, chloroform, etc.; ethers, such as diethyl ether, THF, etc.; and any other solvent that will not react with the fluorinating reagent.

The reaction temperature can range from 0° C. to 90° C. In carrying out the reaction, the difluoroketone can be mixed with the entire charge of the fluorinating reagent or the reagent can be added dropwise to a solution of the difluoroketone. Lewis acid catalysts such as boron trifluoride etherate (BF$_3$.Et$_2$O) or HF can be used to accelerate the reaction. The product obtained is usually a mixture of the desired 1,1,2,2-tetrafluoro compound and the corresponding 1,1,2,4-tetrafluoro isomer. We have found that both the yield and the isomer ratio are highly dependent on the solvent used. Toluene is unexpectedly superior to other organic solvents in producing a high yield of the desired isomer. For example, when THF was used as solvent at 60° C., a 65% yield of 1,1,2,2-tetrafluoro-6-trans-4-propylcyclohexyl)-1,2-dihydronaphthalene was obtained (1,1,2,2-tetrafluoro/1,1,2,4-tetrafluoro=51/49), while when toluene was used as solvent at the same temperature, an 85% yield was obtained (1,1,2,2-tetrafluoro/1,1,2,4-tetrafluoro=90/10) under the same reaction conditions.

In the third step of the process, the mixture of tetrafluoro isomers is reductively defluorinated using a reducing agent in an aqueous ammonia solution, preferably a buffered aqueous ammonia medium. Both tetrafluoro isomers react to form the same vicinal difluoro aromatic product.

The reducing agent in this method can be metallic zinc or other known reducing agents, such as copper, magnesium, or mixtures thereof. The metals typically are used in powder form, but other forms should also be effective. Reducing agents that do not react rapidly with water are preferred. At least one molar equivalent of the reducing agent, based on the amount of starting compound, is needed.

The process of reductive defluorination is preferably carried out in buffered aqueous ammonia with an organic co-solvent, such as THF. The organic co-solvent can be used to make a solution of the tetrafluoro aromatic compound. Other co-solvents that can be used include ethers such as methyl tert-butyl ether; nitriles such as acetonitrile; alcohols such as ethanol; and amides such as DMF. The aqueous ammonia is buffered to a pH <14 and preferably <11 with an ammonium salt; preferably ammonium chloride. Maintaining a pH below 14, minimizes the production of unwanted by-products. For example, when the reaction medium is too basic (i.e., a pH of 14), 1,1,2,2-tetrafluoro dihydronaphthalene is converted to a 1,2,4-trifluoronaphthalene compound as shown in the reaction below:

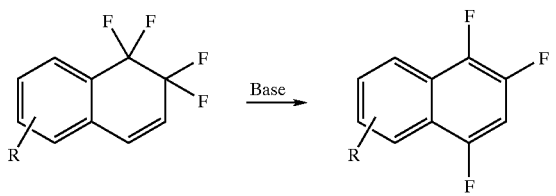

The rate of this reaction has been found to be pH-dependent, and consequently the selectivity to this impurity is significantly reduced as the pH is reduced below 14, especially below 11.

Typically 3.2 ml of ammonium hydroxide and 1.6 ml of organic solvent per mmol of starting compound are appropriate for the reaction.

The reaction can be carried out at temperatures ranging from 0° C. to the boiling point of the solvent; preferably 25 to 45° C.

The reaction can be run in air or more preferably under an inert gas, such as nitrogen.

The reaction can be monitored by methods known in the art to determine completion. For example GC or GC/MS (gas chromatography/mass spectrometry) can be used to determine when the reaction is complete. Reaction times typically range from 2–48 hours.

The vicinal difluoro aromatic product can be isolated from the reaction mixture by methods known in the art. For example, the product can be isolated by filtering the reducing metal, extracting the aqueous layer into an immiscible organic solvent, evaporating the solvent, and purifying the product using chromatography, distillation, and/or recrystallization.

The invention will be further clarified by a consideration of the following examples, which are intended to be purely exemplary of the invention.

EXAMPLE 1

Synthesis of 1,1-difluoro-(trans-4-propylcyclohexyl)-1H-naphthalene-2-one Using DMF Solvent A suspension of 6-(trans-4-propylcyclohexyl) naphthalene-2-ol (30 g, 111.9 mmol) in DMF (180 ml) was treated with Selectfluor reagent (79.9 g, 224.4 mmol) in 5 equal portions at 15 minute intervals. The mixture was stirred for a further 4 hours (h) at room temperature (RT). On completion, the reaction mixture was washed with water (2×100 ml) and NaHCO$_3$ (100 ml), dried (MgSO$_4$), filtered, and evaporated in vacuo. After purification by column chromatography on silica gel (ethyl acetate/hexanes 1/9), the product (33.6 g, 98%) was obtained. Use of DMF unexpectedly resulted in a substantially higher yield of product compared to use of CH$_3$CN in Example 2.

EXAMPLE 2

Synthesis of 1,1-difluoro(trans-4-propylcyclohexyl)-1H-naphthalene-2-one Using Acetonitrile Solvent A suspension of 6-(trans-4-propylcyclohexyl) naphthalene-2-ol (30 g, 111.9 mmol) in CH$_3$CN (225 ml) was treated with Selecifluor reagent (79.9 g, 224.4 mmol) in 5 equal portions at 15 min intervals. The mixture was stirred for a further 4 h at RT. On completion, the reaction mixture was extracted with 100 ml of toluene, washed with water (2×100 ml) and saturated NaHCO$_3$ (100 ml), dried (MgSO$_4$), filtered, and evaporated in vacuo. The residue was chromatographed on silica gel (ethyl acetate/hexanes 1/9) to obtain the product (25.37 g, 74%). MS: m/e=304 (M$^+$)

EXAMPLE 3

Synthesis of 1,1,2,2-tetrafluoro-6-(trans-4-propylcyclohexyl)-1,2-dihydronaphthalene Using Toluene Solvent A solution of 1,1-difluoro-(trans-4-propylcyclohexyl)-1H-naphthalene-2-one (2.0 g, 6.6 mmol) in toluene (5 ml) was heated to 60° C. in a teflon tube under N$_2$. To this solution was added the Deoxo-Fluor reagent dropwise (2.48 g, 2.1 ml, 11.22 mmol). The mixture was heated for a further 5 h. On cooling to 0° C. the solution was treated with 0.5 ml of methanol (MeOH) and saturated NaHCO$_3$. After CO$_2$ evolution ceased the solution was diluted with 20 ml toluene and the organic layer was separated, dried (MgSO$_4$), filtered, and evaporated in vacuo. The residue was purified by chromatography on silica gel (hexanes as solvent) to obtain the pure product (1.82 g, 85% yield as a 90/10 mixture of the title product and the 1,1,2,4-tetrafluoro isomer). MS: m/e 326 (M$^+$).

EXAMPLE 4

Synthesis of 1,1,2,2-tetrafluoro-6-(trans-4-propylcyclohexyl)-1,2-dihydronaphthalene Using THF Solvent A solution of 1,1-difluoro-(trans-4-propylcyclohexyl)-1H-naphthalene-2-one (2.0 g, 6.6 mmol) and Deoxo-Fluor reagent (2.48 g, 2.1 ml, 11.22 mmol) in THF (4 mL) was heated for 3 h at 60° C. in a teflon tube under N$_2$. On cooling to 0° C., the solution was treated with MeOH (0.5 ml) and saturated NaHCO$_3$. After CO$_2$ evolution ceased, the solution was diluted with 20 ml EtOAc and the organic layer was separated, dried (MgSO$_4$), filtered, and evaporated in vacuo. The residue was purified by chromatography on silica gel (hexanes as solvent) to obtain the pure product (1.39 g, 65% yield as a 51/49 mixture of the title product and the 1,1,2,4-tetrafluoro isomer). MS: m/e 326 (M$^+$).

EXAMPLE 5

Synthesis of 1,1-difluoro-6-(trans-4-propylcyclohexyl)-1,2-dihydronaphthalene-2-one A solution containing 6-(trans-4-propylcyclohexyl)-2-naphthol, 100.3 g (0.37 mole), in 200 ml of DMF was added dropwise to a slurry of Selectfluor reagent, 304.5 g (0.86 mole) in 250 ml of DMF while stirring under $N_2$. The temperature of the reaction mixture was maintained below 30° C. After the addition was completed, the reaction mixture was stirred at ambient temperature, and sampled periodically for analysis by gas chromatography. When the GC results showed no detectable starting material, the reaction was terminated. Toluene, 450 ml, and water, 375 ml, were added. The mixture was stirred and then transferred to a separatory funnel. The aqueous layer was withdrawn, and the organic layer was washed with 2×400 ml of water. An orange solid, 106.7 g (94% yield) was recovered after evaporation of the solvent from the organic phase. The product was characterized by GC and NMR analyses. This example shows that purification of the intermediate is not required.

EXAMPLE 6

Synthesis of 1,1,2,2-tetrafluoro-6-(trans-4-propylcyclohexyl)-1,2-dihydronaphthalene 1,1-Difluoro-6-(trans-4-propylcyclohexyl)-1,2-dihydronaphthalene-2-one (47.9 g, 0.16 mole) was dissolved in toluene and charged to a Teflon vessel. The reactor was purged with $N_2$, then sealed and heated to 60° C. When the temperature reached 60° C., Deoxo-Fluor reagent, 49.4 ml (0.27 mole), was added via syringe. The reaction mixture was stirred at 60–65° C. until GC analysis showed that the starting material had been consumed. The mixture was cooled to 10° C., and quenched by adding methanol then neutralized by adding 10% KOH. The mixture was transferred to a separatory funnel, and the aqueous layer was withdrawn. The organic layer was washed with 5% $NaHCO_3$ solution. The product, 48.5 g, was isolated as an oil after evaporation of the solvent and was analyzed by GC and NMR.

EXAMPLE 7

Synthesis of 1,2-difluoro-6-(trans-4-propylcyclohexyl)naphthalene

A mixture of 1,1,2,2-tetrafluoro-6-(trans-4-propylcyclohexyl)-1,2-dihydronaphthalene and 1,1,2,4-tetrafluoro-6-(trans-4-propylcyclohexyl)-1,2-dihydronaphthalene, 10.0 g (30.6 mmol) in THF was stirred with zinc dust (10 g, 153 mmol) and aqueous 30% $NH_4OH$ at ambient temperature. After 27 h, GC analysis showed that the mixture contained <1% of the starting material. The mixture was filtered, and the zinc was washed with hexanes. The filtrate was transferred to a separatory funnel, the phases were separated, and the solvent was evaporated from the organic phase. The weight of product recovered was 8.6 g. GC analysis of the product showed that it contained 0.9% 1,1,2,2-tetrafluoro-6-(trans-4-propylcyclohexyl))-1,2-dihydronaphthalene, 13.4% 1,2,4-trifluoro-6-(trans-4-propylcyclohexyl)naphthalene, and 82% 1,2-difluoro-6-(trans-4-propylcyclohexyl)naphthalene. This example shows that when ammonia is not buffered to reduce the pH, more by-products are formed compared to the reaction in which buffered ammonia is used (Example 8).

EXAMPLE 8

Synthesis of 1,2-difluoro-6-(trans-4-propylcyclohexyl)naphthalene Using Buffered Ammonia A mixture of 1,1,2,2-tetrafluoro-6-(trans-4-propylcyclohexyl)-1,2-dihydronaphthalene and 1,1,2,4-tetrafluoro-6-(trans-4-propylcyclohexyl)-1,2-dihydronaphthalene, 25.6 g (78.4 mmol) in THF was stirred at ambient temperature with zinc dust (25.0 g, 382 mmol) and a solution containing ammonium chloride dissolved in aqueous 30% $NH_4OH$. The reaction was terminated after 48 h. The mixture was filtered, and the zinc was washed with hexanes. The filtrate was transferred to a separatory funnel, the phases were separated, and the solvent was evaporated from the organic phase. The weight of product recovered was 21.9 g. GC analysis of the product showed that it contained 0.2% 1,1,2,2-tetrafluoro-6-(trans-4-propylcyclohexyl)-1,2-dihydronaphthalene, 2.1% 1,2,4-trifluoro-6-(trans-4-propylcyclohexyl)naphthalene, and 93.1% 1,2-difluoro-6-(trans-4-propylcyclohexyl)naphthalene.

EXAMPLE 9

Synthesis of 1,2-difluoro-6-(trans-4-propylcyclohexyl)naphthalene Using a Cu—Zn Catalyst 1,1,2,2-Tetrafluoro-6-(trans-4-propylcyclohexyl)-1,2-dihydronaphthalene, 10.0 g (30.6 mmol) in THF was stirred at ambient temperature with zinc dust (10 g, 153 mmol), copper powder (5.0 g, 79 mmol), and a solution containing ammonium chloride dissolved in aqueous 30% $NH_4OH$. The copper powder was prepared by reduction of copper sulfate pentahydrate with zinc. After 24 h, the reaction was terminated. The mixture was filtered, and the copper-zinc was washed with hexanes. The filtrate was transferred to a separatory funnel, the phases were separated, and the solvent was evaporated from the organic phase. The weight of product recovered was 8.2 g. GC analysis of the product showed that it contained 0.1% 1,1,2,2-tetrafluoro-6-(trans-4-propylcyclohexyl)-1,2-dihydronaphthalene, 1.7% 1,2,4-trifluoro-6-(trans-4-propylcyclohexyl)-naphthalene, and 94% 1,2-difluoro-6-(trans-4-propylcyclohexyl)naphthalene.

EXAMPLE 10

Synthesis of 1,2-difluoronaphthalene from 2-hydroxynaphthalene (a) Formation of 1,1-difluoro-1H-naphthalene-2-one A suspension of 2-hydroxynaphthalene (5.0 g, 34.72 mmol) in DMF (50 ml) under $N_2$ was treated with Selectfluor reagent (24.58 g, 69.44 mmol) in eight equal portions at 15 min intervals. The mixture was stirred for a further 1 h, diluted with 50 ml of ethyl acetate (EtOAc), washed with water (2×25 ml), dried ($MgSO_4$), filtered, and evaporated in vacuo. Purification by flash chromatography on silica gel (1:9 ethyl acetate/hexanes) furnished the product (6.12 g, 98% yield). MS: m/e 180 ($M^+$)

(b) Formation of 1,1,2,2-tetrafluoro-1,2-dihydronaphthalene

To a solution of 1,1-difluoro-1H-naphthalene-2-one (6.12 g, 34 mmol) in toluene (5 ml) under $N_2$ in a teflon tube was added the Deoxo-Fluor reagent (13.15 g, 10.9 ml, 59.5 mmol) and $BF_3.Et_2O$ (440 µL). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene and the organic layer was separated, dried ($MgSO_4$), filtered, and evaporated in vacuo. The residue was purified by chromatography on silica gel (hexanes as solvent) to obtain the pure product (5.84 g, 85% yield as a 90/10 mixture of the title product and the 1,1,2,4-tetrafluoro isomer). MS: m/e 202 ($M^+$)

(c) Formation of 1, 2-difluoronaphthalene

A solution of the tetrafluoro naphthalene, 1,1,2,2-tetrafluoro-1,2-dihydronaphthalene (5.25 g, 25.66 mmol) in THF (15 ml) was treated with 30% aqueous $NH_4OH$ (30 ml) and zinc (8.45 g, 130 mmol) (powder) and stirred under $N_2$ for 4 hours at RT. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 3.99 g (95% yield) of product. MS: m/e 164 ($M^+$)

EXAMPLE 11

Synthesis of 1,2-difluoronaphthalene from 6-bromo-2-hydroxynaphthalene (a) Formation of 6-bromo-1,1-difluoro-1H-naphthalene-2-one A suspension of 6-bromo-2-hydroxynaphthalene (5.0 g, 22.42 mmol) in DMF (25 ml) under $N_2$ was treated with Selecifluor reagent (15.87 g, 44.84 mmol) in eight equal portions at 15 min intervals. The mixture was stirred for a further 1 h, diluted with EtOAc (50 ml), washed with water (2×25 ml), dried ($MgSO_4$), filtered, and evaporated in vacuo. Purification by flash chromatography on silica gel (1:9 ethyl acetate/hexanes) furnished the product (5.51 g, 95% yield). MS: m/e 259 ($M^+$)

(b) Formation of 6-bromo-1,1,2,2-tetrafluoro-1,2-dihydronaphthalene

To a solution of 6-bromo-1,1-difluoro-1H-naphthalene-2-one (5.51 g, 21.27 mmol) in toluene (5 ml) under $N_2$ in a teflon tube was added the Deoxo-Fluor reagent (8.42 g, 7.01 ml, 38.11 mmol) and $BF_3.Et_2O$ (282 μL, 2.24 mmol). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene, and the organic layer was separated, dried ($MgSO_4$), filtered, and evaporated in vacuo. The residue was purified by chromatography on silica gel (hexanes as solvent) to obtain the pure product (4.78 g, 80% yield as a 85/15 mixture of the title product and the 1,1,2,4-tetrafluoro isomer). MS: m/e 281 ($M^+$)

(c) Formation of 1,2-difluoronaphthalene

A solution of the tetrafluoro naphthalene, 6-bromo-1,1,2,2-tetrafluoro-1,2-dihydronaphthalene (4.74 g, 16.80 mmol) in THF (15 ml) was treated with 30% aqueous $NH_4OH$ (30 ml) and zinc (8.45 g, 130 mmol) and stirred under $N_2$ for 24 hours at RT. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 2.62 g (95% yield) of product.

EXAMPLE 12

Synthesis of 9,10-difluoro phenanthrene from 9-phenanthrol (a) Formation of 10,10-difluoro-10H-phenanthrene-9-one A suspension of 9-phenanthrol (2.0 g, 10.31 mmol) in DMF (20 ml) under $N_2$ was treated with Selectfluor reagent (7.30 g, 20.62 mmol) in eight equal portions at 15 min intervals. The mixture was stirred for a further 1 h, diluted with EtOAc (50 ml), washed with water (2×25 ml), dried (MgSO4), filtered, and evaporated in vacuo. Purification by flash chromatography on silica gel (1:9 ethyl acetate/hexanes) furnished the product (2.13 g, 90% yield). MS: m/e 230 ($M^+$)

(b) Formation of 9,9,10,10-tetrafluoro-9,10-dihydrophenanthrene

To a solution of 10,10-difluoro-10H-phenanthrene-9-one (2.13 g, 9.28 mmol) in toluene (5 ml) under $N_2$ in a teflon tube was added the Deoxo-Fluor reagent (3.87 g, 3.2 ml, 17.50 mmol) and $BF_3.Et_2O$ (126 μL, 1.0 mmol). The mixture was heated at 60° C. for 3 h. On cooling to 0° C., the solution was treated with MeOH (0.5 ml) and saturated $NaHCO_3$ (100 ml). After $CO_2$ evolution ceased, the solution was diluted with 20 ml toluene and the organic layer was separated, dried ($MgSO_4$), filtered, and evaporated in vacuo. The residue was purified by chromatography on silica gel (hexanes as solvent) to obtain the pure product (1.96 g 84% yield). MS: m/e 252 ($M^+$)

(c) Formation of 9, 10-difluorophenanthrene

A solution of the 9,9,10,10-tetrafluoro-9,10-dihydrophenanthrene (1.96 g, 7.75 mmol) in THF (15 ml) was treated with 30% aqueous $NH_4OH$ (30 ml) and zinc (2.52 g, 38.75 mmol) and stirred under $N_2$ for 24 hours at room temperature. The reaction was monitored by GC/MS for disappearance of the starting material and found to be complete. The solution was filtered, extracted with hexane (30 ml), and filtered through a short silica column (20 g). The hexane solution was evaporated in vacuo to afford an oil. This crystallized on cooling to room temperature to afford 1.58 g (95% yield) of product.

What is claimed is:

1. A method for making aromatic compounds having two vicinal fluorine atoms comprising:

(a) mixing an electrophilic fluorinating agent with a solution or suspension of a hydroxy aromatic compound in a polar aprotic solvent to form a difluoroketone derivative of an aromatic compound, said hydroxy aromatic compound having one, two or three rings, said rings being separate or fused and said rings optionally containing one or more heteroatoms and one or more substitutions in addition to hydroxy, said difluoroketone derivative having both fluorine atoms on a carbon vicinal to the ketone;

(b) mixing a deoxofluorinating agent with the difluoroketone derivative of (a) in a solvent to form a tetrafluoro derivative of an aromatic compound; and (c) mixing the tetrafluoro derivative of an aromatic compound of (b) in an organic solvent with a reducing agent in aqueous ammonia to form an aromatic compound containing two vicinal fluorine atoms.

2. The method of claim 1 wherein said one or more optional substitutions on said rings is one or more of a halogen atom, a C1 to C20 alkyl, a C5–C10 cycloalkyl, a C6 to C12 aryl, an amino, a nitro, a C1 to C10 alkyl ether or thioether, a C1 to C10 alkyl ester, a $CF_3$, a $R'SO_2O$,

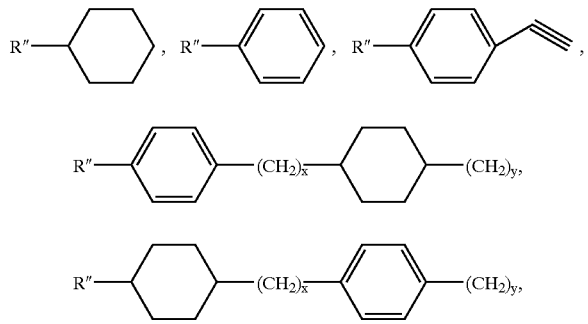

-continued

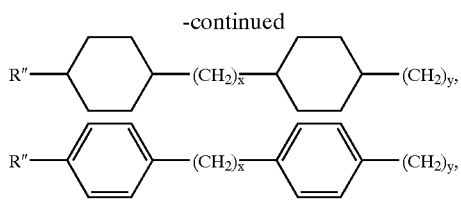

where R' is $CF_3$, a C1 to C20 alkyl, a substituted or unsubstituted C5 to C10 cycloalkyl, or a substituted or unsubstituted C6 to C12 aryl, wherein the substitution on the cycloalkyl or aryl can be a C1 to C20 alkyl or a C5 to C8 cycloalkyl; R" is a C1–C10 saturated or unsaturated alkyl; x is an integer from 0 to 10, and y is an integer from 0 to 10.

3. The method of claim 1 wherein the solvent in (a) is dimethylformamide, the solvent in step (b) is toluene, and the solvent in step (c) is tetrahydrofuran.

4. The method of claim 1 wherein the reducing agent in step (c) is zinc, magnesium, copper, or mixtures thereof.

5. The method of claim 4 wherein the reducing agent is zinc.

6. The method of claim 1 wherein the aqueous ammonia in step (c) is buffered with an ammonium salt to maintain a pH of less than 14.

7. The method of claim 6 wherein the aqueous ammonia is buffered with ammonium chloride to maintain a pH of less than 11.

8. The method of claim 1 wherein the hydroxy aromatic compound is 6-(trans-4-propylcyclohexyl)naphthalene-2-ol.

* * * * *